United States Patent [19]

Tamai et al.

[11] Patent Number: 4,547,462

[45] Date of Patent: Oct. 15, 1985

[54] PROCESS FOR PREPARING SUBSTANCE HAVING CARCINOSTATIC AND IMMUNOSTIMULATING ACTIVITY

[75] Inventors: Kenzo Tamai, Kanazawa; Isamu Saikawa, Toyama; Takashi Yasuda, Toyama; Shohachi Murakami, Toyama; Toyoo Maeda, Kanazawa; Hisatsugu Tsuda, Toyama; Hiroshi Sakai, Takaoka; Masatoshi Sugita, Toyama; Yoshiko Yamamoto, Namerikawa; Hisashi Minami; Takako Hori, both of Toyama, all of Japan

[73] Assignee: Toyama Chemical Co., Ltd., Tokyo, Japan

[21] Appl. No.: 523,438

[22] Filed: Aug. 16, 1983

[30] Foreign Application Priority Data

Aug. 17, 1982 [JP] Japan .................. 57-142439

[51] Int. Cl.$^4$ .................. C12P 19/00; C12R 1/01

[52] U.S. Cl. .................. 435/72; 435/822; 424/118

[58] Field of Search .................. 435/72

[56] References Cited

U.S. PATENT DOCUMENTS 4,477,437 10/1984 Tamai et al. .................. 435/116

FOREIGN PATENT DOCUMENTS 53-130496 12/1978 Japan .................. 435/72

Primary Examiner—Lionel M. Shapiro
Attorney, Agent, or Firm—Oblon, Fisher, Spivak, McClelland & Maier

[57] ABSTRACT

This invention relates to a process for producing a TF-500 substance having carcinostatic and immunostimulating activities, which comprises subjecting organisms belonging to the Fusobacterium genus to extraction treatment with a dialkyl sulfoxide and obtaining said TF-500 substance from the resulting extract.

11 Claims, 9 Drawing Figures

10μ

PROCESS FOR PREPARING SUBSTANCE HAVING CARCINOSTATIC AND IMMUNOSTIMULATING ACTIVITY

BACKGROUND OF THE INVENTION

1. Field of the Invention

This invention relates to a novel process for producing a carcinostatic substance, and more precisely, this invention relates to a novel process for producing a carcinostatic substance having the undermentioned properties or a salt thereof, which comprises subjecting organisms belonging to the *Fusobacterium* genus to extraction treatment with a dialkyl sulfoxide and obtaining a TF-500 substance or a salt thereof from the resulting extract.

2. Description of the Prior Art

In recent years, there has come to be extensively used, as a remedy for patients with various types of cancer, a remedy comprising enhancing the immunological function of the host and obtaining a carcinostatic effect with the assistance of the immunological function.

The present inventors have examined the pharmacological activity of components obtained by the extraction treatment with a dialkyl sulfoxide of the organisms belonging to the *Fusobacterium* genus isolated from the oral cavity to find that a specific component obtained from the extract has a carcinostatic activity; that said component has an indirect carcinostatic activity by increasing the host-mediated antitumor activity or the immunity of the host and utilizing the assistance of the immunity; and that said component is very low in toxicity, and investigated processes for producing the same and completed the present invention.

SUMMARY OF THE INVENTION

This invention is to provides a novel process which comprises subjecting organisms belonging to the *Fusobacterium* genus to extraction treatment with a dialkyl sulfoxide and obtaining a carcinostatic substance from the resulting extract.

This invention is further described in the following paragraphs.

DESCRIPTION OF THE INVENTION

As the organisms utilized in this invention, any TF-500 substance-producing bacteria belonging to the *Fusobacterium* genus may be used, and, for example, those belonging to *Fusobacterium nucleatum* are preferably used. Specifically, *Fusobacterium nucleatum* TF-031 (FERM 5077; ATCC 31647) and strains which are considered to have said properties in a general knowledge of microbiology, namely, spontaneous mutants or artificially modified strains are used.

The bacteriological properties of *Fusobacterium nucleatum* TF-031 are as follows:

(I) Form
  (1) Form of the cells: spindle-shaped (FIG. 1)
  (2) Polymorphism of the cells: absent
  (3) Motility: absent
  (4) Spores: absent
  (5) Gram stain: Gram-negative
  (6) Acid resistance: negative
(II) Growing conditions in a culture medium
  (1) TF-a agar plate and slant culture medium
    External form: a round shape
    Size: about 1 mm
    Protuberance: hemispherical shape
    Structure: dewdrop-like
    Surface: smooth
    Edges: smooth
    Color: milky yellowish white
    Transparency: opaque
  (2) TF-a liquid culture medium
    Degree of growth: vigorous
    Turbidity: coagulum
    Precipitate: none
    Growth of surface: none, no growth to a depth of about 5 mm
    Gas: none
(III) Physiological properties
  (1) Production of hydrogen sulfide: +
  (2) Reduction of nitrates: −
  (3) Production of butyric acid: +
  (4) Production of indole: +
  (5) Urease: −
  (6) Catalase: −
  (7) Hydrolysis of starch: −
  (8) Behavior to oxygen: anaerobic
  (9) Production of ammonia: +
  (10) Production of carbon dioxide: +
  (11) Range for growth: pH 5.0–8.5, temperature 30°–45° C.
  (12) Production of gas from saccharides: L-arabinose (−), D-xylose (−), D-glucose (−), D-mannose (−), D-fructose (−), D-galactose (−), malt sugar (−), sucrose (−), trehalose (−), sorbitol (−), mannitol (−), inositol (−), glycerol (−), starch (−)

The process for the production of carcinostatic substance TF-500 is conducted, for example, in the following manner:

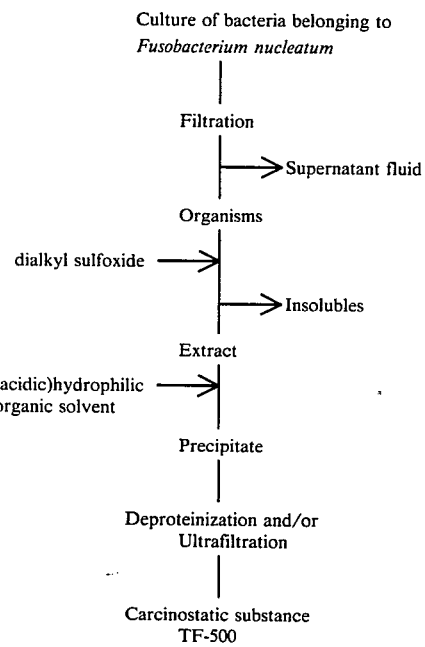

The above-mentioned production process is explained below.

(I) Culture of bacteria

The culture of bacteria belonging to the *Fusobacterium* genus is carried out by a conventional method for culturing anaerobic bacteria. That is to say, a culture medium containing a nitrogen source such as bovine brain-heart extracts, various peptones, or the like; a vitamine source such as yeast extract, or the like; an inorganic salt such as sodium chloride, or the like; a carbon source such as glucose, lactose, or the like; a reducing agent such as L-cystine, sodium sulfite, sodium thioglycolate or the like, is adjusted to a pH of 5 to 8.5, preferably 6.5 to 7.5, with an aqueous sodium hydroxide solution and the bacteria are inoculated on the culture medium, after which steady-state culture or stirring culture is carried out under anaerobic conditions at 30° to 45° C., preferably 32° to 37° C., for 1 to 5 days, preferably 1 to 4 days. In particular, it is desirable to use the culture medium described in Table 1 (hereinafter referred to as the TF culture medium). However, the brain-heart-infusion which is a bovine brain-heart extract is not always necessary as a nitrogen source and may be replaced by a heart infusion which is a bovine heart extract, a beef extract, a fish extract, a corn steep liquor, or the like. Among the various peptones, proteose peptone and phytone peptone are not always necessary, and the trypticase peptone may be replaced by polypeptone.

When agar is not used, it is desirable to carry out stirring culture.

TABLE 1

| Constituents of culture medium (g/l) | TF-a | TF-b | TF-c | TF-d | TF-e | TF-f |
| --- | --- | --- | --- | --- | --- | --- |
| Trypticase peptone | 17 | 17 | 17 | 17 | 17 | 17 |
| Phytone peptone | 3 | 3 | 1.5 | — | — | — |
| Proteose peptone | 10 | 5 | 5 | — | — | — |
| Brain-heart-infusion | 35 | 17.5 | — | — | — | — |
| Heart infusion | — | — | 25 | 20 | 10 | 15 |
| Yeast extract | 3 | 3 | 3 | 3 | 3 | 3 |
| Sodium chloride | 7.5 | 7.5 | 7.5 | 7.5 | 7.5 | 7.5 |
| Glucose | 6 | 6 | 6 | 12 | 12 | 12 |
| Lactose | 5 | 5 | 5 | 10 | 10 | 10 |
| L-Cystine | 0.25 | 0.5 | 0.5 | — | — | — |
| Sodium sulfite | 0.1 | 0.1 | 0.1 | 0.1 | 0.1 | 0.1 |
| Sodium thioglycolate | 0.5 | 0.5 | 0.5 | 0.5 | 0.5 | 0.5 |
| Agar | 0 or 0.7 | 0 or 0.7 | 0 or 0.7 | 0 or 0.7 | 0 or 0.7 | 0 or 0.7 |
| Dipotassium hydrogenphosphate | — | — | 2.5 | 2.5 | 2.5 | 2.5 |

(II) Collection of the organisms from the culture

A supernatant fluid is removed from the culture obtained above to get the organisms. For the removal of a supernatant fluid, a conventional method, for example, centrifugation and a filtration method using a filter aid, such as Celite (trade name of Johns-Manville, U.S.A.), may be used. And, the obtained organisms are washed with physiological salt solution and then dried in a conventional manner, for example, lyophilization, or are washed with physiological salt solution and subsequently with a hydrophilic organic solvent such as ethanol, acetone, or the like, in a short time and then dried in a conventional manner, such as air-drying or the like, to obtain the dried organisms. And, if necessary, the dried organisms are pulverized to obtain the dried powder.

(III) Extraction procedure

To the above obtained dried organisms is added a dialkyl sulfoxide, for example, dimethyl sulfoxide, diethyl sulfoxide, or the like, preferably dimethyl sulfoxide in a proportion of 10 to 50 ml per gram of the dried organisms. The extraction treatment is carried out with stirring at room temperature to 80° C. for 30 minutes to several days, preferably, at about 65° C. for 3 to 5 hours. Subsequently, insolubles are removed by a conventional procedure such as decantation, centrifugation, filtration, or the like. And, to the extract obtained above is added a hydrophilic organic solvent, for example, a ketone such as acetone, diethyl ketone, methyl ethyl ketone, or the like, or an alcohol such as methanol, ethanol, isopropanol, or the like, in a quantity more than 5 times that of the extract (volume/volume) at a low temperature. Preferably, the hydrophilic organic solvent is added under acidic conditions, for example, acetone is added together with hydrochloric acid and the resulting mixture is allowed to stand at about 4° C. for several hours to several days.

The precipitate is separated in a conventional manner. Then, the thus obtained precipitate is subjected to deproteinization treatment or ultrafiltration treatment alone or to a combination of the two.

When the organisms are washed with physiological salt solution and then dried by lyophilization, the deproteinization treatment or the ultrafiltration treatment may not be included to obtain a carcinostatic substance TF-500 or a salt thereof.

(IV) Deproteinization, ultrafiltration and collection of the objective substance The precipitate obtained above is subjected to the deproteinization treatment and subsequently the ultrafiltration treatment, or to the deproteinization treatment alone, or to the ultrafiltration treatment alone, to obtain a carcinostatic substance TF-500 or a salt thereof.

For the deproteinization treatment, methods known in the art may be used. When the deproteinization is carried out by a treatment with a proteolytic enzyme, the precipitate thus obtained is dissolved or suspended in water or a buffer solution, a proteolytic enzyme is added to the resulting solution or suspension, and the enzyme-treatment is conducted in a conventional manner.

As the proteolytic enzymes, there may be used pronase, papain, trypsin, chemotrypsin, and the like. Pronase and trypsin are preferred. It is preferable that, prior to or during the enzyme-treatment, the aqueous solution be adjusted to and maintained at a pH of 7 to 8. For this purpose, there may be used sodium hydroxide, potassium hydroxide, sodium carbonate, ammonium carbonate, sodium hydrogencarbonate, and the like. In order to prevent the putrefaction of the reaction mixture during the enzyme-treatment, it is desirable to add a small quantity of an organic solvent such as chloroform, toluene, or the like. The enzyme is usually used in an amount of about 1 to 4% by weight based on the weight of the powder (solid) to be subjected to the enzyme treatment.

The above enzyme-treatment is usually carried out at 30° to 40° C. for 1 to 72 hours, preferably 24 to 48 hours. It may also be conducted by first adding, for example, about 1 to 2% by weight of an enzyme to a powder (solid) and subjecting the powder (solid) to enzyme-treatment treatment for 1 to 24 hours and subsequently adding about 1 to 2% by weight of the enzyme again for further enzyme-treatment.

After the above enzyme-treatment, insolubles are, if necessary, removed by a procedure such as centrifugation, filtration, or the like, after which from the water-soluble portion thus obtained is collected a carcinostatic substance TF-500.

The collection of TF-500 from the water-soluble portion may be first conducted by at least one of fractionation depending upon pH, separate precipitation from a hydrophilic organic solvent, fractionation with an ion exchanger, and the like, and then by ultrafiltration (the treatment may be repeated twice). Specifically, the present carcinostatic substance TF-500 is obtained by adjusting the pH of the above water-soluble portion to preferably, not more than 2.5 (if necessary, trichloroacetic acid may be added), removing the resulting precipitate, adding to the soluble portion a hydrophilic organic solvent such as ethanol so that its concentration becomes 30 to 80%, preferably 60 to 80%, by volume, collecting the resulting precipitate which is the fraction of the objective substance, subsequently treating, if necessary, this precipitate with an anion exchange resin such as Dowex 1 type (trade name), Amberlite IRA-400 (trade name), DEAE-Sephadex (trade name), DEAE-Cellulose (trade name), or the like (this treatment may be conducted several times) to collect the unadsorbed fractions, and then concentrating and desalting an aqueous solution of the precipitate obtained or the fractions obtained by ultrafiltration (nominal molecular weight cutoff: 50,000-200,000), by means of, for example, Ultrafiltration Memberane UK-50 (nominal molecular weight cutoff: 50,000), Ultrafiltration Membrane UK-200 (nominal molecular weight cutoff: 200,000) or the like (Ultrafiltration Membrane UK-50 and UK-200 are trade names for ultrafiltration membranes of Toyo Roshi Kabushiki Kaisha), and drying the concentrated and desalted product. 0.2% Aqueous solution of this TF-500 (weight/volume) is transparent.

As explained above, instead of the deproteinization treatment and subsequent ultrafiltration treatment, the above-explained deproteinization treatment or ultrafiltration treatment can be carried out alone.

The thus obtained carcinostatic substance TF-500 has the following properties, and may be converted to a pharmaceutically acceptable salt according to a conventional method. Specifically, said pharmaceutically acceptable salts include, for example, alkali metal salts such as sodium salts, potassium salts, and the like and alkaline earth metal salts such as magnesium salts, calcium salts, and the like.

The properties of the carcinostatic substance TF-500 are as follows:

(a) Grayish white-light brown powder.

(b) It has a carcinostatic and immunostimulating activity.

(c) It is soluble in water but insoluble in methanol, ethanol, acetone, benzene, chloroform, ethylacetate and diethyl ether.

(d) It has no clear melting point, and begins to decompose at about 180° C., and remarkably decomposes above 195° C.

(e) Its infrared absorption spectrum obtained by the KBr method has absorption bands in the vicinities of 3500–3200, 2920, 2850, 1660–1600, 1580–1520, 1460–1400, 1380–1360, 1120–1100, 1080–1000, 970 and 840–800 $cm^{-1}$.

(f) Its ultraviolet absorption spectrum of its aqueous solution at a pH of 7.0 shows a strong absorption at the absorption edge, and shows an absorption peak in the vicinity of 246–280 nm.

(g) It is positive in Molish reaction, phenolsulfuric acid reaction, anthrone-sulfuric acid reaction, indolehydrochloric acid reaction and Lowry-Folin's reaction, but negative in ninhydrin reaction.

(h) Elementary analysis values C: 38–47% H: 5–7% N: 1–4%.

(i) Its saccharide content as determined by a phenol-sulfuric acid method is about 12–30% by weight in terms of glucose, and its protein content as determined by Lowry-Folin's method is about 10% by weight or less in terms of bovine serum albumin.

The pharmacological activities of the present carcinostatic substance TF-500 are as follows:

(I) Effect of TF-substance on cell viability (Colony-forming Assay)

Based on the method of Kim. J. H. et al. (Cancer Res. 25, 698 (1965), HeLa S-3 cells were cultured in Eagle's MEM supplemented with 10% calf serum for 3 to 5 days at 37° C., after which the culture was removed, and a PBS(−) solution (an aqueous solution containing 8.0 g/l of sodium chloride, 0.2 g/l of potassium chloride, 1.15 g/l of disodium hydrogenphosphate, and 0.2 g/l of potassium dihydrogenphosphate) containing 0.01% by weight of ethylenediaminetetraacetic acid and 0.1% by weight of trypsin was added by pipetting to the cell layer obtained to form a suspension. The cell suspension thus obtained was diluted with Eagle's MEM supplemented with 20% calf serum so that it contained 300 cells per ml. One milliliter of this cell suspension was cultured at 37° C. for 24 hours in a $CO_2$-incubator, and to the resulting culture was then added the carcinostatic substance TF-500 obtained in Example 1 which appears hereinafter so that the concentration became 250, 500, 1000 μg/ml. Two experiments were conducted, one of which was the case of adding serum (20%; volume/volume) to the culture, and the other was the case of adding no serum. After treatment for 24 hours, the cells were washed with the serum-free culture, and to the cells was then added the culture having added thereto 20% calf serum, after which the cells were cultured for 6 days in a $CO_2$-incubator. After the culturing, the cells were fixed by ethanol and stained with a Giemsa-staining solution, and the resulting colonies were counted to determine the viability of the cells. The results obtained are shown in Table 2, in which the cell viability was determined by the following equation:

$$\text{Cell viability (\%)} = \frac{\text{Number of colonies in the treated group}}{\text{Number of colonies in the untreated group}} \times 100$$

TABLE 2

| Concentration of carcinostatic substance (μg/ml) | Cell viability (%) | |
|---|---|---|
| | serum-free culture medium | Serum-added culture medium |
| 0 | 100 | 100 |
| 250 | 103.8 | 103.2 |
| 500 | 100.2 | 98.5 |
| 1000 | 55.2 | 97.1 |

(II) Immunostimulating activity

Three ICR strain mice (female, 6 weeks old) for each group were used. 5 μg, 50 μg and 500 μg/kg of the test substance were intraperitoneally administered to the mice. Twenty-four hours after the administration, 0.2 ml of a carbon suspension prepared by mixing 1 ml of Perikan Drawing Ink 17 Black (manufactured by Günther-Wagner Co., Ltd.) with 2 ml of physiological salt solution containing 3% by weight of gelatin was intravenously injected into the mouse tail and 1, 5, 10 and 15 minutes after the injection, 0.02 ml of the blood was sampled from the orbit by using a hematocrit capillary coated with heparin, and immediately diluted and hemolyzed with 1.6 ml of a 0.1% by weight aqueous sodium carbonate solution. This suspension was subjected to colorimetry at 675 nm, and the phagocytotic index, namely K value, was determined from the equation of Halpern et al.

To the mice in the control group was administered 0.2 ml of physiological salt solution.

$$K = \frac{\log C_0 - \log C}{t - t_0}$$

wherein $C_0$=concentration of carbon in the blood at the time $t_0$, and C=concentration of carbon in the blood at the time t.

The results are as shown in Table 3.

TABLE 3

| Dose (μg/kg) | Average K value |
| --- | --- |
| 5 | 0.0418 ± 0.0089 |
| 50 | 0.0560 ± 0.0016 |
| 500 | 0.0561 ± 0.027 |
| Control | 0.0276 ± 0.0020 |

Note: *The carcinostatic substance obtained in Example 1 was used.

(III) Antitumor activity against Sarcoma-180 cells

Sarcoma 180 cells were subcutaneously transplanted to ICR strain mice (female, 6 weeks old) at the armpit in an amount of $1 \times 10^7$ cells per mouse. Subsequently, each of the test substances was dissolved in a 5% aqueous glucose solution and 0.2 ml of each of the resulting solutions was intraveneously administered to the mice once a day on the tenth and twelfth day from the transplanting of the carcinoma cells. To the control group, 0.2 ml of a 5% aqueous glucose solution was administered in the same manner as above. The results are shown in Table 4.

TABLE 4

| Dose (mg/kg) | Mean tumor weight ± S.E. (g) | Haemorrhagic necrosis of tumor (Day 14) | T/C*[3] (%) (Day 14) |
| --- | --- | --- | --- |
| 0.5*[1] | 3.4 ± 0.7 | 5/5 | 53 |
| 1.0*[1] | 3.6 ± 0.7 | 4/5 | 56 |
| 0.5*[2] | 4.1 ± 2.4 | 3/5 | 63 |
| 1.0*[2] | 5.0 ± 1.9 | 3/5 | 79 |
| Control | 6.4 ± 2.7 | 0/5 | 100 |

Note:
*[1] The carcinostatic substance obtained in Example 1 was used.
*[2] The carcinostatic substance obtained in Example 2 was used.

*[3] T/C (%) = $\frac{\text{Mean tumor weight of mice in the substance-administered group}}{\text{Mean tumor weight of mice in the control group}} \times 100$ (IV) Acute toxicity $LD_{50}$ value for mice (ICR strain, female, 6 weeks old, intravenous administration) of TF-500 is more than 10 mg/kg.

As is evident from the above-mentioned pharmacological experiments, the TF-500 substance of this invention is useful as carcinostatic agent, and can be expected to have activities against various cancerous diseases.

The TF-500 substance or its pharmaceutically acceptable salt of this invention may be used after shaping them into various pharmaceutical forms such as oral drugs, injections, suppositories, or the like.

When they are used as oral drugs, the oral drugs may contain various excipients, and may be formed into capsules, tablets, powder, or granules. When they are used as injections, the injections may be any of subcutaneous injections, intramuscular injections, and intravenous injections, and they are used in the form of a suspension, a solution or a powder which is dissolved in physiological saline or the solution containing a glucose or a local anesthetics when used. The dosage of the TF-500 substance or its pharmaceutically acceptable salt of this invention is properly selected depending on the conditions of a patient, though, in general, it is desirable to administer the same in a dosage for an adult of 0.001 to 0.1 mg/kg once a day or several times a day, and as to the administration method, they are administered preferably by, oral, subcutaneous, intramuscular, or intravenous injection or injection into the affected part.

This invention is further explained in detail below referring to Examples, Preparation Examples and the accompanying drawings, in which drawings, FIG. 1 shows a microsopic photograph indicating the form of *Fusobacterium nucleatum* TF-031 used in this invention;

EXAMPLE 1

Figure 1:
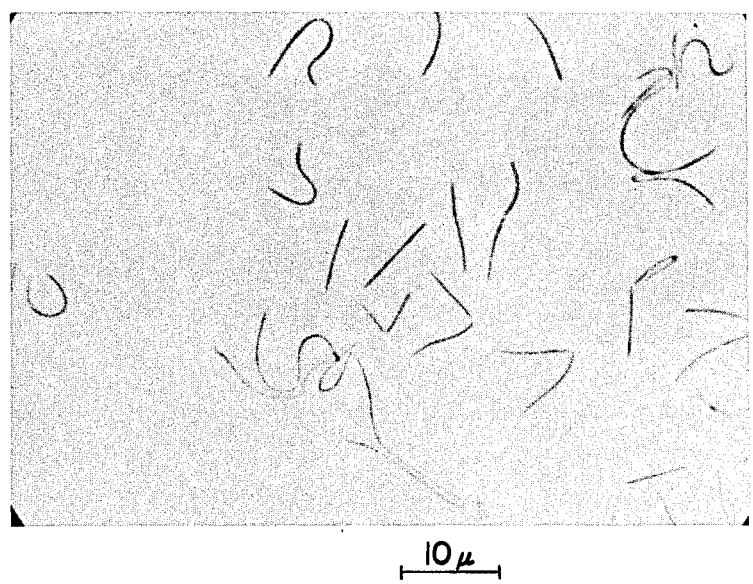

(1) In a 90-liter jar fermenter (MSJ-U type, manufactured by Marubishi Rika Kenkyusho) was placed 70 liters of a TF-f culture medium containing 1,190 g of trypticase petone, 1,050 g of heart infusion, 210 g of yeast extract, 525 g of sodium chloride, 840 g of glucose, 700 g of lactose, 7 g of sodium sulfite, 35 g of sodium thioglycolate and 175 g of dipotassium hydrogenphosphate, and the culture medium was adjusted to pH 7.5 with 4 N aqueous sodium hydroxide solution. The culture medium was sterilized for 15 min at 118° C. After cooling the culture medium, a nitrogen gas was passed through the same at a rate of 250 ml/min for 1 hr. Into this culture medium was inoculated about 900 ml of a precultured solution of *Fusobacterium nucleatum* TF-031 (FERM-5077, ATCC-31647) previously prepared by culturing it in a TF-f culture medium having the same composition as above. The cells were cultured for 4 days at 33° C. with stirring (90 r.p.m.) while introducing a nitrogen gas at a rate of 250 ml/min.

(2) A 12-liter portion of the culture thus obtained was subjected to centrifugation ($4 \times 10^3$ r.p.m., 10 min) to collect the organisms, and the organisms were washed with 1 liter of physiological salt solution, and subsequently defatted and washed with 1 liter of ethanol and 1 liter of acetone in this order, and then dried to obtain 14.2 g of the organisms. The organisms were suspended in 300 ml of dimethyl sulfoxide, and subjected to extraction with stirring for 4 hours while heating the suspension at 65° C. Subsequently, the suspension was filtered by suction to obtain a filtrate. To this filtrate were added 2 liters of acetone and 8 ml of conc. hydrochloric acid, and the resulting mixture was then allowed to stand for 2 days to settle and age the resulting precipitate. This precipitate was collected by centrifugation ($4 \times 10^3$ r.p.m., 10 min) (748 mg).

(3) The 748 mg of the precipitate thus obtained was dissolved in 15 ml of water, and the resulting solution was adjusted to pH 7.8–8.0 with ammonium carbonate. To this solution were added two 7.5-mg portions of Pronase E (trade name of Kaken Kagaku; 1,000,000 tyrosine units/g) at 30-minute interval, and several drops of toluene was then added thereto, after which the resulting mixture was subjected to enzymetreatment at 37° C. for 24 hours. To the thus treated mixture was added hydrochloric acid to adjust the pH to 1, and ethanol was then added thereto so that the ethanol concentration became 80% by volume. The resulting mixture was subjected to centrifugation ($4 \times 10^3$ r.p.m., 10 min) and the resulting precipitate was collected (288.6 mg).

(4) The 288.6 mg of the precipitate thus obtained was dissolved in 50 ml of water and the resulting solution was concentrated to 5 ml by ultrafiltration using Ultrafiltration Membrane UK-50, and 45 ml of water was added to the concentrated solution thus obtained, after which the thus diluted solution was again concentrated to 5 ml by ultrafiltration using Ultrafiltration Membrane UK-50. This concentrated solution was filtered through a Millipore Filter (trade name for a membrane filter of Japan Millipore Limited) having a pore diameter of 0.2 μm, and then freeze-dried, to obtain 264 mg of the freeze-dried carcinostatic substance TF-500.

Figure 2:
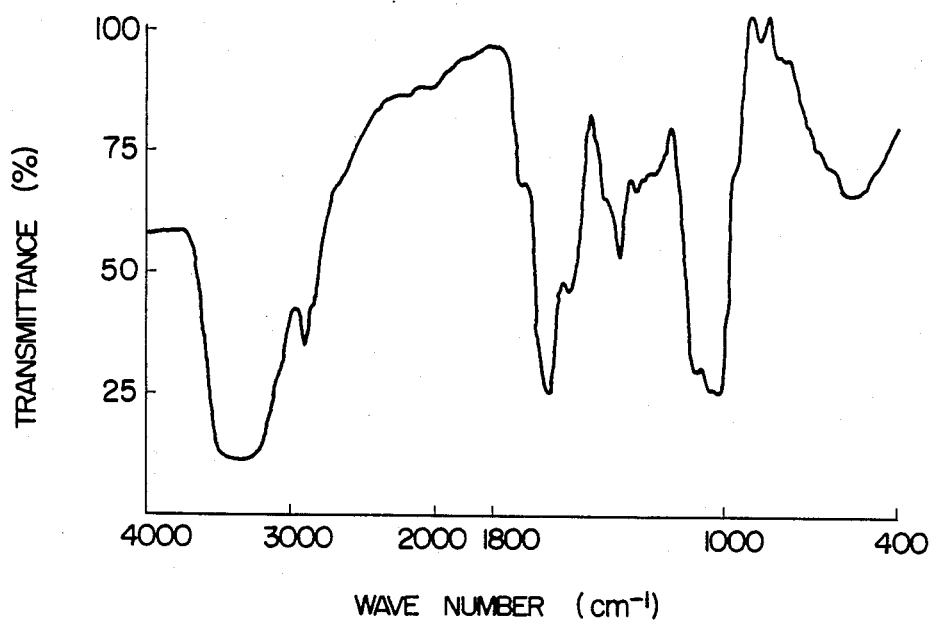
FIG. 2 shows an infrared absorption spectrum of the TF-500 obtained in Example 1, which appears hereinafter.
Figure 3:
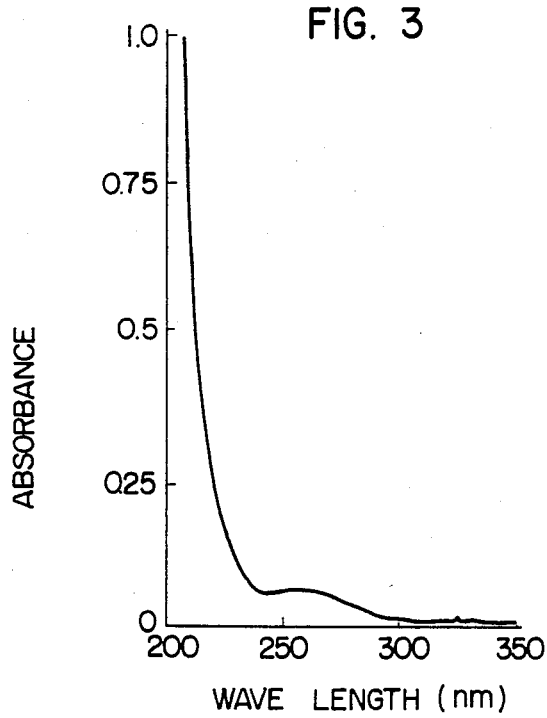
FIG. 3 shows an ultraviolet absorption spectrum of said substance.

The carcinostatic substance TF-500 thus obtained had the properties mentioned hereinbefore and the infrared absorption spectrum shown in FIG. 2 and the ultraviolet absorption spectrum shown in FIG. 3.

EXAMPLE 2

(1) From 70 liters of the culture obtained in Example 1-(1), organisms were collected by filtration through Hyflo Super Cel (trade nmae of Johns-Manville, U.S.A.), and the resulting mixture of the organisms with Hyflo Super Cel was washed with 20 liters of physiological salt solution, and subsequently defatted and washed with 3 liters of ethanol and 3 liters of acetone in this order, to obtain 3.2 kg of dried said mixture. A 320-g portion of this mixture was suspended in 400 ml of dimethyl sulfoxide, and the resulting suspension was subjected to extraction with stirring for 4 hours while heating the same at 65° C. Subsequently, the suspension was filtered by suction to collect a filtrate, and 2.5 liters of acetone and 10 ml of conc. hydrochloric acid were added thereto, after which the resulting mixture was allowed to stand at 4° C. for 2 days to settle and age the precipitate. The precipitate was collected by centrifugation ($4 \times 10^3$ r.p.m., 10 min) (94 mg).

(2) In 50 ml of water was dissolved the 94 mg of the precipitate thus obtained, and the resulting solution was concentrated to 5 ml by ultrafiltration using Ultrafiltration Membrane UK-50, and 45 ml of water was added to the concentrated solution thus obtained, after which the thus diluted solution was again concentrated to 5 ml by ultrafiltration using Ultrafiltration Membrane UK-50.

The thus concentrated solution was filtered through a Millipore filter having a pore diameter of 0.2 μm, and then freeze-dried to obtain 62.6 mg of the freeze-dried carcinostatic substance TF-500.

Figure 4:
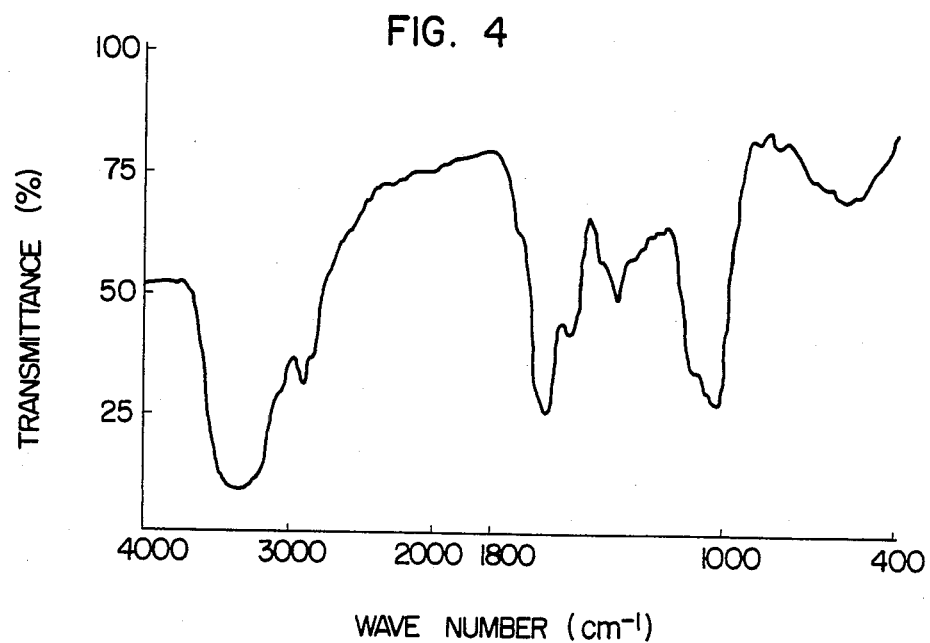
FIG. 4 shows an infrared absorption spectrum of the TF-500 obtained in Example 2, which appears hereinafter.
Figure 5:
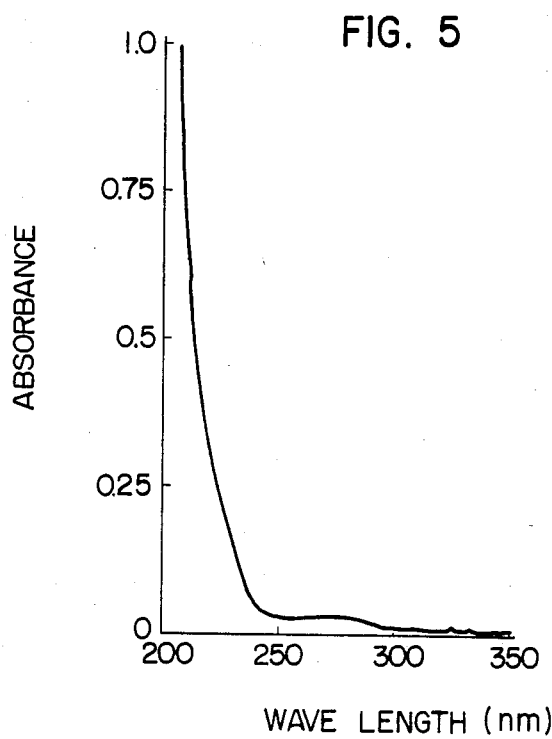
FIG. 5 shows an ultraviolet absorption spectrum of said substnace.

The carcinostatic substance TF-500 thus obtained had the properties mentioned hereinbefore, and had the infrared absorption spectrum shown in FIG. 4 and the ultraviolet absorption spectrum shown in FIG. 5.

EXAMPLE 3

(1) A 7.2-liter portion of the culture obtained in Example 1-(1) was subjected to centrifugation ($5 \times 10^3$ r.p.m., 10 min) to collect the organisms, and they were freeze-dried. A 3.5-g portion of the thus freeze-dried organisms was suspended in 100 ml of physiological salt solution, and the resulting suspension was adjusted to pH 8.0 with 2 N aqueous sodium hydroxide solution, stirred for 3 hours, then allowed to stand for 24 hours, and thereafter subjected to centrifugation ($5 \times 10^3$ r.p.m., 10 min.) to remove the supernatant. To the precipitate obtained was added 100 ml of physiological salt solution, and the resulting mixture was adjusted to pH 8.0 with 2 N aqueous sodium hydroxide solution. The mixture was stirred for 2 hours and then subjected to centrifugation ($5 \times 10^3$ r.p.m., 10 min) to remove the supernatant. Subsequently, the precipitate obtained was washed with three 50-ml portions of ethanol, one 50-ml portion of acetone and one 50-ml portion of diethyl ether in this order (the removal of the washings was carried out by centrifugation ($5 \times 10^3$ r.p.m., 10 min)), and then dried to obtain dried organisms. The organisms were pulverized to obtain a powder thereof. To the powder was added 70 ml of dimethyl sulfoxide, and the resulting mixture was subjected to extraction with stirring at 63°–65° C. for 4 hours, and then to suction filtration to collect a filtrate. To this filtrate were added 536 ml of acetone and 1 ml of conc. hydrochloric acid, and the resulting mixture was allowed to stand at 4° C. for 24 hours to settle and age the precipitate. The precipitate was collected by centrifugation ($5 \times 10^3$ r.p.m., 10 min) (269 mg).

(2) To the 269 mg of the precipitate thus obtained was added 2.7 ml of water, and the resulting mixture was adjusted to pH 8.0 with 1 N aqueous sodium hydroxide solution, after which water was added thereto to adjust the final volume to 4 ml. To the mixture was added 2.7 mg of Pronase E (1,000,000 tyrosine units/g), and the resulting mixture was subjected to enzyme-treatment at 37° C. for 1 hour. Further, 2.7 mg of Pronase E and several drops of toluene were added thereto, and the resulting mixture was subjected to enzyme-treatment at 37° C. for 24 hours. Insolubles were removed from the thus treated mixture by centrifugation ($5 \times 10^3$ r.p.m., 10 min), and to the solution obtained was added 2 N hydrochloric acid to adjust the pH thereof to 1.0, after which ethanol was added thereto so that the ethanol concentration became 80% by volume. The precipitate thus obtained was collected by centrifugation ($5 \times 10^3$ r.p.m., 10 min) (78.5 mg).

(3) To the 78.5 mg of the precipitate thus obtained was added 20 ml of water and the resulting mixture was adjusted to pH 7 with 1 N aqueous sodium hydroxide solution. Subsequently, the resulting mixture was concentrated to 5 ml by ultrafiltration using Ultrafiltration Membrane UK-50, and 45 ml of water was added to the concentrated solution thus obtained, after which the thus diluted solution was again concentrated to 5 ml by ultrafiltration using Ultrafiltration Membrane UK-50. To the concentrated solution thus obtained was added 45 ml of water and the thus diluted solution was concentrated to 5 ml by ultrafiltration using Ultrafiltration Membrane UK-50. This concentrate was filtered through a membrane filter having a pore diameter of 0.2 μm (Toyo Roshi Kabushiki Kaisha TM-4), and then freeze-dried to obtain 65 mg of freeze-dried carcinostatic substance TF-500.

Figure 6:
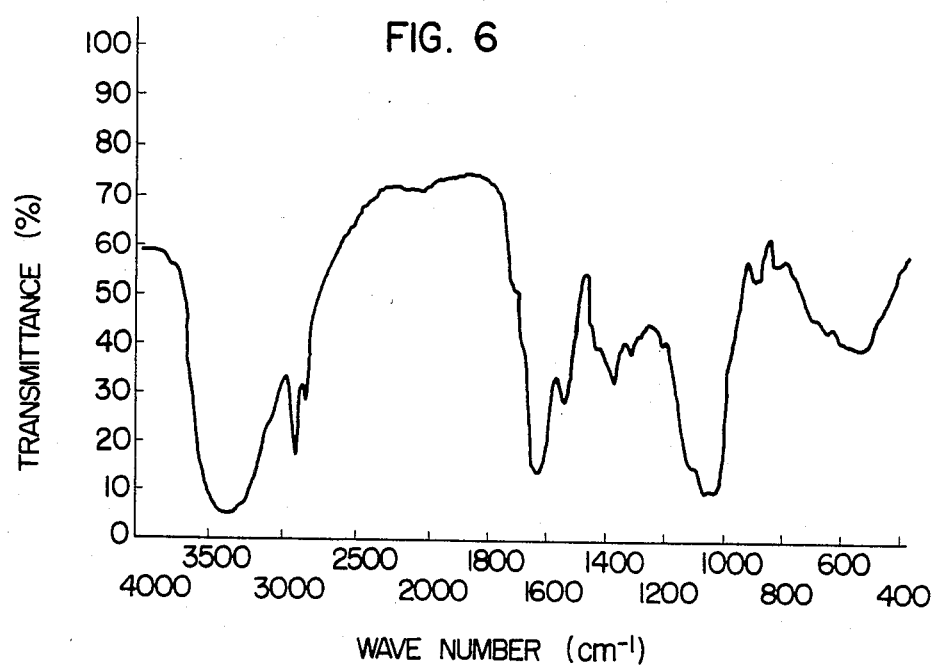
FIG. 6 shows an infrared absorption spectrum of the TF-500 obtained in Example 3, which appears hereinafter.
Figure 7:
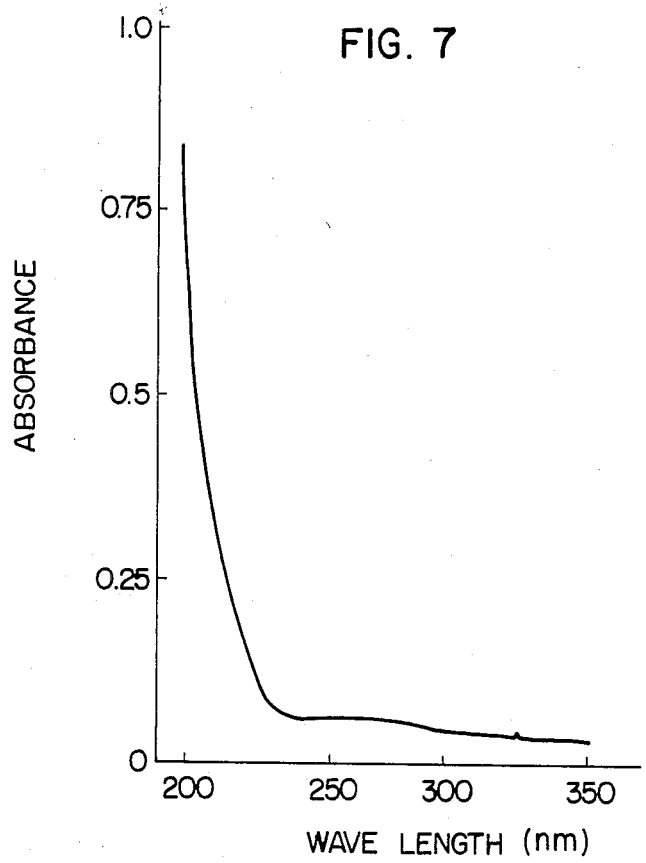
FIG. 7 shows an ultraviolet absorption spectrum of said substance.

The carcinostatic substance TF-500 thus obtained had the properties mentioned hereinbefore and had the infrared absorption spectrum shown in FIG. 6 and the ultraviolet absorption spectrum shown in FIG. 7.

EXAMPLE 4

(1) A 10-liter portion of the culture obtained in Example 1-(1) was centrifuged ($5 \times 10^3$ r.p.m., 10 min) to collect the organisms. To the organisms was added 500 ml of physiological salt solution, and the resulting mixture was stirred for 30 minutes, and then centrifuged ($5 \times 10^3$ r.p m., 10 min) to collect the precipitate. This procedure was repeated twice. To the precipitate thus obtained was added 500 ml of physiological salt solution, and the resulting mixture was stirred for 30 minutes, thereafter adjusted to pH 8.0 with 1 N aqueous sodium hydroxide solution and then stirred for 30 minutes. Subsequently, the mixture was centrifuged ($5 \times 10^3$ r.p.m., 10 min), and defatted and washed with 500 ml of physiological salt solution. Subsequently, the mixture was centrifuged ($5 \times 10^3$ r.p.m., 10 min) to obtain the precipitate. The precipitate obtained was washed with one 500-ml portion of physiological salt solution, one 300-ml portion of ethanol and one 300-ml portion of acetone in this order (the removal of the washings was carried out by centrifugation ($5 \times 10^3$ r.p.m., 10 min)) and then dried to obtain dried organisms. The organisms thus obtained were pulverized to obtain a powder thereof. To this powder was added 160 ml of dimethyl sulfoxide, and the resulting mixture was then subjected to extraction with stirring at 63°–65° C. for 4 hours. Subsequently, the mixture was filtered by suction to obtain a filtrate, and to the filtrate were added 1.2 liters of acetone and 4.2 ml of conc. hydrochloric acid, after which the resulting mixture was allowed to stand at 4° C. for 24 hours to settle and age the precipitate. This precipitate was centrifuged ($5 \times 10^3$ r.p.m., 10 min) to collect the precipitate (246 mg).

(2) To the 246 mg of the precipitate thus obtained was added 5 ml of water, and the resulting mixture was adjusted to pH 7.8 with 1 N aqueous sodium hydroxide solution. To the mixture was added 5 mg of Pronase E (1,000,000 tyrosine units/g) and the mixture was subjected to enzyme-treatment at 37° C. for 30 minutes, after which 1 N aqueous sodium hydroxide solution was added to the mixture to adjust the pH to 7.8, after which 5 mg of Pronase E and several drops of toluene were added again thereto. The resulting mixture was subjected to enzyme-treatment at 37° C. for 24 hours. To the treated mixture was added 1 N hydrochloric acid to adjust the pH to 1.0, and the resulting mixture was allowed to stand for 2 hours and subsequently centrifuged ($5 \times 10^3$ r.p.m., 10 min) to obtain the supernatant. To the supernatant obtained was added ethanol so that the ethanol concentration became 80% by volume. And the resulting mixture was allowed to stand for 2 hours and centrifuged ($5 \times 10^3$ r.p m., 10 min) to collect the precipitate settled (98 mg).

(3) To the 98 mg of the precipitate thus obtained was added 20 ml of water and the resulting mixture was adjusted to pH 7 with 1 N aqueous sodium hydroxide solution. Subsequently, the resulting mixture was concentrated to 5 ml by ultrafiltration using Ultrafiltration Membrane UK-50, and 45 ml of water was added to the concentrated solution thus obtained, after which the thus diluted solution was again concentrated to 5 ml by ultrafiltration using Ultrafiltration Membrane UK-50. To the concentrated solution thus obtained was added 45 ml of water and the thus diluted solution was concentrated to 5 ml by ultrafiltration using Ultrafiltration Membrane UK-50. The concentrate obtained was filtered through a membrane filter having a pore diameter of 0.2 μm (Toyo Roshi Kabushiki Kaisha TM-4), and then freeze-dried to obtain 83 mg of the freeze-dried carcinostatic substance TF-500.

Figure 8:
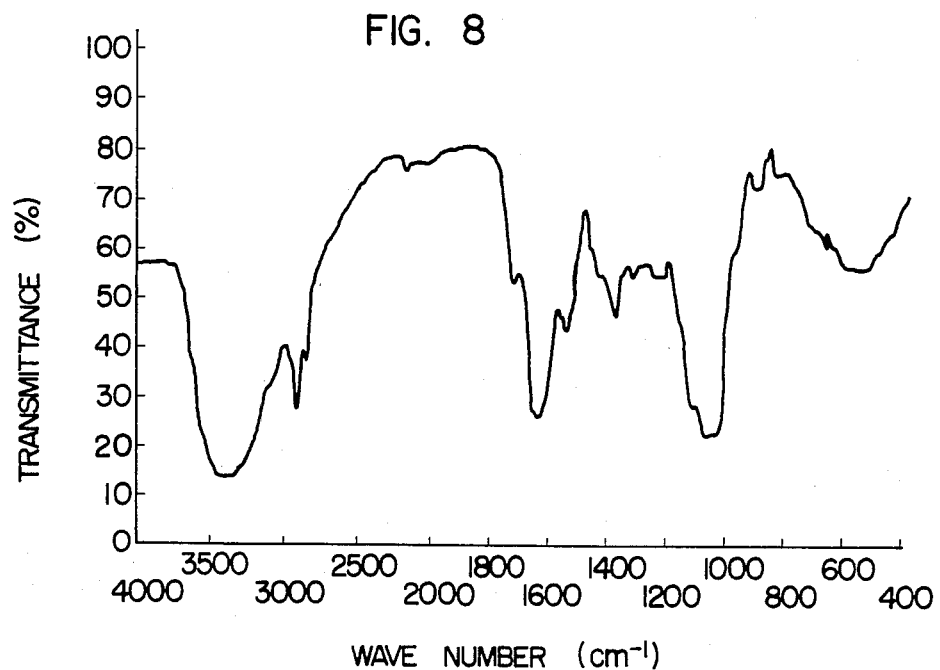
FIG. 8 shows an infrared absorption spectrum of the TF-500 obtained in Example 4, which appears hereinafter.
Figure 9:
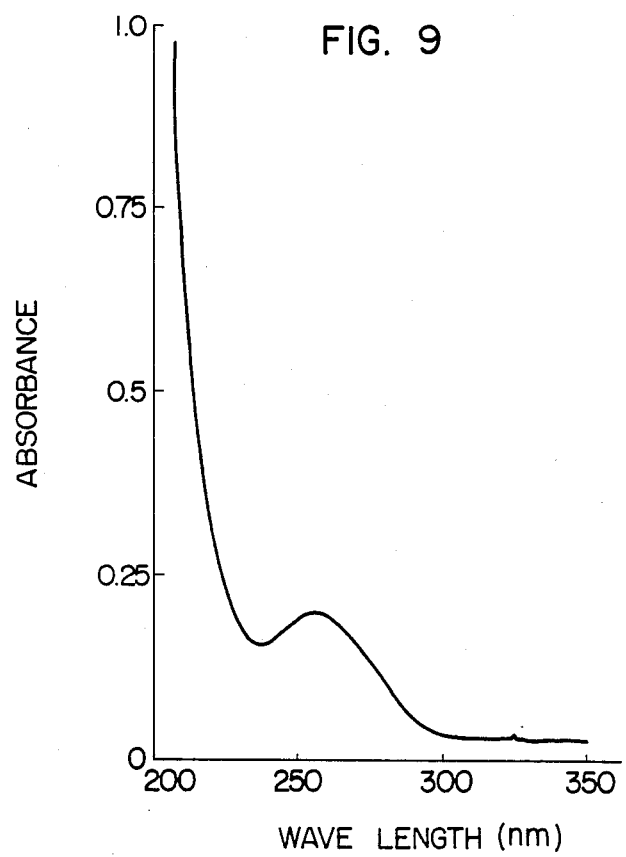
FIG. 9 shows an ultraviolet absorption spectrum of said substance.

The carcinostatic substance TF-500 thus obtained had the properties mentioned hereinbefore and had the infrared absorption spectrum shown in FIG. 8 and the ultraviolet absorption spectrum shown in FIG. 9.

PREPARATION EXAMPLE 1

An aqueous solution having a pH of 7.0 to 7.5 containing the carcinostatic substance TF-500 obtained in Example 1 was charged into a vial, and freeze-dried to obtain a freeze-dried carcinostatic substance TF-500 preparation having a 0.5 or 1 mg unit. This is dissolved, when used, in sterile physiological salt solution, a 0.5% lidocaine solution, a 0.5% aqueous glucose solution, or the like, and the resulting solution is used as an injection.

PREPARATION EXAMPLE 2

An aqueous solution having a pH of 7.0 to 7.5 containing the carcinostatic substance TF-500 obtained in Example 2 was charged into a vial, and freeze-dried to obtain a freeze-dried carcinostatic substance TF-500 preparation having a 0.5 or 1 mg unit. This is dissolved, when used, in sterile physiological salt solution, a 0.5% lidocaine solution, a 0.5% aqueous glucose solution, or the like, and the resulting solution is used as an injection.

PREPARATION EXAMPLE 3

An aqueous solution having a pH of 7.0 to 7.5 containing the carcinostatic substance TF-500 obtained in Example 3 was charged into a vial, and freeze-dried to obtain a freeze-dried carcinostatic substance TF-500 preparation having a 0.5 or 1 mg unit. This is dissolved, when used, in sterile physiological salt solution, a 0.5% lidocaine solution, a 0.5% aqueous glucose solution, or the like, and the resulting solution is used as an injection.

PREPARATION EXAMPLE 4

An aqueous solution having a pH of 7.0 to 7.5 containing the carcinostatic substance TF-500 obtained in Example 4 was charged into a vial, and freeze-dried to obtain a freeze-dried carcinostatic substance TF-500 preparation having 0.5 or 1 mg unit. This is dissolved, when used, in sterile physiological salt solution, a 0.5% lidocaine solution, a 0.5% aqueous glucose solution, or the like, and the resulting solution is used as an injection.

What is claimed is:

1. A process for preparing a carcinostatic substance TF-500 having the following properties or a salt thereof, which comprises subjecting *Fusobacterium nucleatum* ATCC 31647 or mutants thereof to extraction treatment with a dialkyl sulfoxide and collecting the said substance from the extract:

(a) Grayish white-light brown powder,
    (b) It has a carcinostatic and immunostimulating activity,
    (c) It is soluble in water but insoluble in methanol, ethanol, acetone, benzene, chloroform, ethyl acetate and diethyl ether,
    (d) It has no clear melting point, and begins to decompose at about 180° C. and remarkably decomposes above 195° C.,
    (e) The infrared absorption spectrum obtained by the KBr method has absorption bands in the vicinities of 3500–3200, 2920, 2850, 1660–1600, 1580–1520, 1460–1400, 1380–1360, 1120–1100, 1080–1000, 970 and 840–800 $cm^{-1}$,
    (f) The ultraviolet absorption spectrum of its aqueous solution at a pH of 7.0 shows a strong absorption at the absorption edge, and shows an absorption peak in the vicinity of 246–280 nm,
    (g) It is positive in Molisch reaction, phenolsulfuric acid reaction, anthrone-sulfuric acid reaction, indole-hydrochloric acid reaction and Lowry-Folin's reaction, but negative in ninhydrin reaction,
    (h) Elementary analysis values C: 38–47%, H: 5–7%, N: 1–4%,
    (i) The saccharide content as determined by a phenolsulfuric acid method is about 12–30% by weight in terms of glucose, and its protein content as determined by Lowry-Folin's method is about 10% by weight or less in terms of bovine serum albumin.

2. The process of claim 1, wherein the microorganisms are
    (a) subjected to an extraction treatment with a dialkyl sulfoxide,
    (b) a hydrophilic organic solvent is added to the resulting extract,
    (c) the precipitate thus obtained is subjected to deproteinization treatment, and
    (d) then to ultrafiltration treatment.

3. The process of claim 2, wherein the dialkyl sulfoxide is dimethyl sulfoxide.

4. The process of claim 2 or 3, wherein the hydrophilic organic solvent is acetone.

5. The process of claim 2, wherein the deproteinization treatment is an enzyme-treatment with a proteolytic enzyme.

6. The process of claim 5, wherein the proteolytic enzyme is a pronase.

7. The process of claim 1, wherein the *Fusobacterium* microorganisms
    (a) are subjected to an extraction treatment with a dialkyl sulfoxide,
    (b) a hydrophilic organic solvent is added to the resulting extract, and
    (c) the precipitate thus obtained is ultrafiltered.

8. The process of claim 7, wherein the dialkyl sulfoxide is dimethyl sulfoxide.

9. The process of claim 7 or 8, wherein the hydrophilic organic solvent is acetone.

10. The process of claim 2 wherein the ultrafiltration treatment is carried out with an ultrafilter having a nominal molecular weight cutoff of 50,000 to 200,000.

11. The process of claim 1, wherein the *Fusobacterium nucleatum* organisms are
    (a) subjected to an extraction treatment with a dialkyl sulfoxide;
    (b) a hydrophilic organic solvent is added under acidic conditions to the resulting extract in a quantity more than 5 times that of the extract (volume/volume);
    (c) the precipitate formed is subjected to deproteinization treatment with a pronase;
    (d) an alcohol is added to the treated fluid so that the alcohol concentration becomes 30 to 80% by volume;
    (e) the precipitate formed is collected and subjected to ultrafiltration and then filtered through a membrane filter; and then
    (f) the filtrate is freeze-dried to obtain the carcinostatic substance.

* * * * *